(12) United States Patent
James et al.

(10) Patent No.: US 8,877,244 B2
(45) Date of Patent: Nov. 4, 2014

(54) STABILIZED PESTICIDAL GRANULES

(75) Inventors: John R. James, Greensboro, NC (US);
Andrew Pearson, Greensboro, NC (US);
Johnny D. Reynolds, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/155,955

(22) Filed: Jun. 22, 2011

(65) Prior Publication Data
US 2011/0245079 A1 Oct. 6, 2011

Related U.S. Application Data

(63) Continuation of application No. 11/682,438, filed on Mar. 6, 2007, now abandoned.

(60) Provisional application No. 60/779,514, filed on Mar. 6, 2006.

(51) Int. Cl.
| | | |
|---|---|---|
| A61K 9/14 | (2006.01) | |
| A61K 9/16 | (2006.01) | |
| A61K 33/34 | (2006.01) | |
| A01N 59/16 | (2006.01) | |
| A01N 59/06 | (2006.01) | |
| A01N 55/02 | (2006.01) | |
| A01N 47/28 | (2006.01) | |
| C05C 9/00 | (2006.01) | |
| C05D 9/00 | (2006.01) | |
| C05B 7/00 | (2006.01) | |
| B01J 19/08 | (2006.01) | |
| C05C 1/00 | (2006.01) | |
| C05C 1/02 | (2006.01) | |
| A01N 41/10 | (2006.01) | |
| C05G 3/02 | (2006.01) | |

(52) U.S. Cl.
CPC . *C05G 3/02* (2013.01); *A01N 41/10* (2013.01)
USPC .......... 424/489; 424/490; 424/638; 424/641; 424/646; 424/682; 504/126; 504/148; 71/28; 71/31; 71/36; 71/58; 71/59

(58) Field of Classification Search
None
See application file for complete search history.

(56) References Cited

U.S. PATENT DOCUMENTS

| | | | |
|---|---|---|---|
| 6,924,250 B2 * | 8/2005 | Cornes .......................... | 504/136 |
| 2005/0202972 A1 * | 9/2005 | Piper et al. .................... | 504/190 |
| 2007/0225169 A1 * | 9/2007 | Hopkinson et al. ........... | 504/118 |
| 2008/0039329 A1 * | 2/2008 | Hopkinson et al. ........... | 504/362 |

* cited by examiner

*Primary Examiner* — Alton Pryor
(74) *Attorney, Agent, or Firm* — Brian D. McAlhaney

(57) ABSTRACT

The present invention provides a stabilized pesticidal composition comprising at least one granular substrate material containing at least one metal chelate of 2-(2'-nitro-4'-methylsulphonylbenzoyl)-1,3-cyclohexanedione, a method of producing a stabilized granular pesticidal composition which comprises incorporating a metal chelate of 2-(2'-nitro-4'-methylsulphonylbenzoyl)-1,3-cyclohexanedione in to or on to a granular substrate material; and a method of killing or controlling weeds or unwanted vegetation (without damaging beneficial plants and or seeds) which comprises applying a herbicidally effective amount of the stabilized granular pesticide composition of the invention to the foliage, tissue or locus of the weeds or unwanted vegetation.

16 Claims, No Drawings

STABILIZED PESTICIDAL GRANULES

This application is a continuation of U.S. Ser. No. 11/682,438, filed Mar. 6, 2007, which claims priority to U.S. 60/779,514 filed Mar. 6, 2006, the contents of which are incorporated herein by reference.

FIELD OF THE INVENTION

The present invention relates to granular pesticidal compositions, to their preparation and to their use. In particular, the present invention relates to granular pesticidal compositions having improved chemical stability on solid substrates used for broadcast application.

BACKGROUND

The protection of crops from weeds and other undesired vegetation that inhibits crop growth is a constantly recurring problem in agriculture, horticulture and other plant cultivation practices. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. Commercial herbicides and some that are still in development are described in The Pesticide Manual, 13$^{th}$ Edition, published 2003 by the British Crop Protection Council.

Many herbicides also damage crop plants. The control of weeds in a growing crop therefore requires the use of so-called 'selective' herbicides, which are chosen to kill the weeds while leaving the crop undamaged. In practice, few herbicides are fully selective, in that they will kill all the weeds and leave the crop untouched at a particular application rate. The use of most selective herbicides is actually a balance between applying enough herbicides to acceptably control most of the weeds and causing only minimal crop damage.

Herbicides may be formulated as wettable powders, water dispersible granules, suspension concentrates, emulsifiable concentrates, powders or dusts, flowables, solutions, suspensions, controlled release forms such as microcapsules, or as dry spreadable or broadcast granules. Herbicides can be co-formulated with other pesticides such as other herbicides, insecticides or fungicides. The choice of formulation type can be influenced by the mode of application. Both formulation type and mode of action for any given selective herbicide may affect both its activity and selectivity. Accordingly, the optimum formulation for any particular selective herbicide will depend upon the mode of application and nature of the plants and any other pests to be controlled.

For certain agricultural, horticultural, and other pest control applications it is often desirable to formulate pesticides as dry spreadable or broadcast granules, as opposed to wettable powders or water dispersible granules that are designed for admixing in large volumes of water such as tank mixes and ultimately sprayed upon sites to be treated. The challenge to deliver chemically stable products for these two approaches can be different.

Selective herbicides formulated as dry spreadable granules are important commercial products because of their ability to eliminate undesirable vegetation in large areas of cultivated vegetation and their ease of application, either by hand or a mechanical means. For example, a practical and labor-saving approach to selective herbicide delivery in areas such as golf courses, parks, lawns, gardens and woodlands has been broadcast application of granular herbicide products via rotary spreader.

Broadcast granular herbicides can be a selective herbicide applied to an inert material, like clay, peanut hull or ground corn cobs, or can be a combination fertilizer/herbicide, wherein the selective herbicide is applied to a fertilizer material, i.e., a "weed and feed" composition.

In a granular form, a selective herbicide is impregnated into, absorbed or coated onto an inert granular carrier or a granular fertilizer material. The granular herbicide product is supplied in a plastic bag, a plastic drum, or a fiber keg. The granular herbicide product is applied to vegetation by directly spreading herbicide granules onto the vegetation at a suitable dosage rate.

One important class of selective herbicides is the triketone class which includes those compounds disclosed, inter alia, in U.S. Pat. Nos. 4,780,127, 4,938,796, 5,006,158 and 5,089,046 the disclosures of which are incorporated herein by reference. One known triketone herbicide is 2-(2'-nitro-4'-methylsulphonylbenzoyl)-1,3-cyclohexanedione. A challenge that is seen with 2-(2'-nitro-4'-methylsulphonylbenzoyl)-1,3-cyclohexanedione, when used in the acid form, is chemical stabilization in certain environments, in a liquid state, in a liquid state applied on or to a solid carrier and on or in a solid carrier. Granule formulations containing the acid form of 2-(2'-nitro-4'-methylsulphonylbenzoyl)-1,3-cyclohexanedione are known (University of Maryland Department of Natural Resource Science and Landscape Architecture: Turfgrass Pathology, Weed Science and Physiology Research Summaries (2005), p. 19).

In addition to the acid form, another known form of 2-(2'-nitro-4'-methylsulphonylbenzoyl)-1,3-cyclohexanedione is as a metal chelate, for example a copper chelate. These metal chelates are disclosed, inter alia, in U.S. Pat. No. 5,912,207 (the disclosure of which is incorporated herein by reference) where they are shown to have unexpectedly superior stability in certain environments when compared to unchelated 2-(2'-nitro-4'-methylsulphonylbenzoyl)-1,3-cyclohexanedione. The '207 patent addresses stabilization of products to be diluted and applied as liquids. Stabilization of chelated 2-(2'-nitro-4'-methylsulphonylbenzoyl)-1,3-cyclohexanedione formulated in a solid form for spreadable application (as opposed to liquid application) is not specifically disclosed in the '207 patent. Stabilising a cyclohexanedione a solid substrate is different to stabilising it in a liquid medium, because it is necessary to block the surface interaction between the reactive granule and the compound itself.

There is a need to develop granular 2-(2'-nitro-4'-methylsulphonylbenzoyl)-1,3-cyclohexanedione compositions with improved stability on long term storage. The present invention provides such stabilized granular 2-(2'-nitro-4'-methylsulphonylbenzoyl)-1,3-cyclohexanedione compositions.

SUMMARY OF THE INVENTION

Accordingly, the present invention provides a stabilized pesticidal composition comprising at least one granular substrate material containing at least one metal chelate of 2-(2'-nitro-4'-methylsulphonylbenzoyl)-1,3-cyclohexanedione.

The granular substrate can be an inert material, e.g., a clay, ground corn cobs or peanut hulls and/or can be a fertilizer material, e.g., urea/formaldehyde fertilizers, urea, potassium chloride, ammonium compounds, phosphorus compounds, sulfur, similar plant nutrients and micronutrients, and mixtures and combinations thereof, both synthetic and naturally occurring organic and inorganic materials.

In addition to metal chelated 2-(2'-nitro-4'-methylsulphonylbenzoyl)-1,3-cyclohexanedione, the inventive stabilized pesticide composition may contain other pesticides such as herbicides, insecticides, growth regulators and fungicides, or other additives such as binders, surfactants, inert fillers or bioavailable minerals and plant nutrients absorbed, impregnated, or coated onto the granular substrate.

The present invention further provides a method of producing a stabilized granular pesticidal composition which comprises incorporating a metal chelate of 2-(2'-nitro-4'-methylsulphonylbenzoyl)-1,3-cyclohexanedione in to a granular substrate material; as well as a method of killing or controlling weeds or unwanted vegetation which comprises applying a herbicidally effective amount of the stabilized granular pesticide composition of the invention to the foliage, tissue or locus of the weeds or unwanted vegetation.

The stabilized herbicidal granules described herein are relatively easy to formulate, ship, store, and apply. Granular formulations offer significant advantages in packaging, ease of handling and safety, relative to liquid formulations. The granules typically have a particle size in the range of about 0.1 to about 30 mm, particularly between about 0.25 to about 20 mm, and more particularly between about 0.5 to about 15 mm, although sizes outside of this range can be used.

DETAILED DESCRIPTION OF THE INVENTION

Cyclohexanedione Compound

The compound 2-(2'-nitro-4'-methylsulphonylbenzoyl)-1,3-cyclohexanedione is a herbicide, known for its ability to control a wide spectrum of broadleaf weeds at a wide range of growth stages when applied post-emergence on corn. It is typically used at a low rate (100-150 grams of active ingredient per hectare) to control weeds which are present at application and which emerge for up to four weeks afterwards. Once applied, 2-(2'-nitro-4'-methylsulphonylbenzoyl)-1,3-cyclohexanedione is rapidly absorbed by the leaves, shoots, roots and seeds. In susceptible weeds, 2-(2'-nitro-4'-methylsulphonylbenzoyl)-1,3-cyclohexanedione disrupts carotinoid biosynthesis, which is an essential process for plant growth, and this leads to plant death. Unlike weeds, corn plants are able to tolerate 2-(2'-nitro-4'-methylsulphonylbenzoyl)-1,3-cyclohexanedione by rapidly breaking down the active compound into inactive compounds. The active cyclohexanedione compound has the following formula:

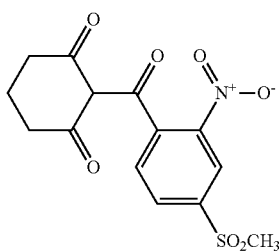

(I)

Metal Chelates of 1,3-cyclohexanediones

Metal chelates of 2-(substituted benzoyl)-1,3-cyclohexanedione compounds including 2-(2'-nitro-4'-methylsulphonylbenzoyl)-1,3-cyclohexanedione are described, inter alia, in U.S. Pat. No. 5,912,207, the disclosure of which is incorporated herein by reference. In one embodiment, suitable metal chelates of 2-(2'-nitro-4'-methylsulphonylbenzoyl)-1,3-cyclohexanedione have the general structure:

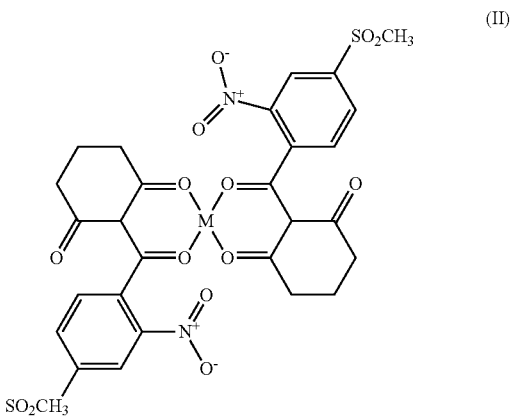

(II)

wherein M represents a di- or trivalent metal ion such as $Cu^{+2}$, $Co^{+2}$, $Zn^{+2}$, $Ni^{+2}$, $Ca^{+2}$, $Al^{+3}$, $Ti^{+3}$ and $Fe^{+3}$.

Herbicidal metal chelates of 2-(2'-nitro-4'-methylsulphonylbenzoyl)-1,3-cyclohexanedione for use in this invention may be prepared by the methods described in the aforementioned United States Patent, or by the application and adaptation of known methods used or described in the chemical literature.

As noted above, metal ions which may be useful in forming the metal chelate compounds of the present invention include di- or trivalent metal ions such as $Cu^{+2}$, $Co^{+2}$, $Zn^{+2}$, $Ni^{+2}$, $Ca^{+2}$, $Al^{+3}$, $Ti^{+3}$ and $Fe^{+3}$. The selection of a particular metal ion to form the metal chelate compound will depend upon the strength of the metal chelate complex desired. Without being bound by theory, it appears as if the strength of the metal chelate complex is directly related to the release rate of 2-(2'-nitro-4'-methylsulphonylbenzoyl)-1,3-cyclohexanedione from the metal chelate complex, which in turn is related to the stability of the metal chelate within the granular compositions of this invention. Those skilled in the art will be able to readily determine the appropriate metal ion for use with a specific granular composition without undue experimentation. Among the suitable metal ions are divalent transition metal ions such as $Cu^{+2}$, $Ni^{+2}$, $Zn^{+2}$ and $Co^{+2}$, more particularly $Cu^{+2}$ and $Zn^{+2}$ and most particularly $Cu^{+2}$.

Any appropriate salt which would be a source of a di- or trivalent metal ion may be used to form the metal chelate of the dione compound in accordance with this invention. Particularly suitable salts include: chlorides, sulfates, nitrates, carbonates, phosphates and acetates.

The stability of the 2-(2'-nitro-4'-methylsulphonylbenzoyl)-1,3-cyclohexanedione metal chelates is pH dependent. The pH can be between about 2 and about 7, with an acidic pH of less than about 6 being suitable for most metals. Generally, it is believed that for $Cu^{+2}$ chelate compositions, the pH should be between about 4 and 6; for $Co^{+2}$ between about 3 and 5; and for $Ni^{+2}$ and $Zn^{+2}$, about 5. The optimum pH for a particular metal chelate composition can be determined using routine experimental techniques known in the art.

An excess of metal ion in the final formulation can increase the chemical stability of the resulting chelate. For divalent metals, the stoichiometric molar ratio of 2-(2'-nitro-4'-methylsulphonylbenzoyl)-1,3-cyclohexanedione to metal ion is 2:1. Thus, the minimum amount of metal ion to be added to the 2-(2'-nitro-4'-methylsulphonylbenzoyl)-1,3-cyclohexanedione to produce the metal chelate is an amount sufficient to provide a molar ratio of 2-(2'-nitro-4'-methylsulphonylbenzoyl)-1,3-cyclohexanedione to metal ion of 2:1. However, amounts in excess of the stoichiometric amount may enhance the chemical stability of the 2-(2'-nitro-4'-methylsulphonylbenzoyl)-1,3-cyclohexanedione, and a molar ratio of 2-(2'-nitro-4'-methylsulphonylbenzoyl)-1,3-cyclohexanedione to metal ion of between about 2:1 and 2:5 is useful in this regard, with a molar ratio of between about 2:1 and 2:3 being particularly noted. Preferably the molar ratio is about 2:3. Without being bound by theory, such amounts appear to stabilize the 2-(2'-nitro-4'-methylsulphonylbenzoyl)-1,3-cyclohexanedione from decomposition.

As used herein, the designation 2-(2'-nitro-4'-methylsulphonylbenzoyl)-1,3-cyclohexanedione includes any enolic tautomeric forms that may give rise to geometric isomers. Furthermore, in certain cases, the various substituents and or chelated forms may contribute to optical isomerism and/or stereoisomerism. All such tautomeric forms, racemic mixtures and isomers are included within the scope of the present invention.

Granules

The granular substrate materials useful in the stabilized pesticidal compositions of the invention typically serve as a solid carrier for the at least one metal chelate of 2-(2'-nitro-4'-methylsulphonylbenzoyl)-1,3-cyclohexanedione. Suitable granular substrate materials include, for example, inert materials, fertilizer materials, or a mixture thereof.

Inert materials (i.e. non-N, P, and K containing components) that can be used to formulate the granular substrate include, but are not limited to, dried clay, calcium carbonate, brick, pumice, pyrophyllite, kaolin, dolomite, plaster, wood flour, ground corn cobs, ground peanut hulls, sugars, sodium chloride, sodium sulfate, sodium silicate, sodium borate, magnesia, mica, iron oxide, zinc oxide, titanium oxide, antimony oxide, cryolite, vermiculite calcinated lime, gypsum, perlite, diatomaceous earth, bentonite clay, calcium sulfate, and mixtures thereof. Examples of inert granular substrates suitable for preparing the stabilized pesticidal compositions of the invention are found in U.S. Pat. Nos. 5,041,410; 5,219,818; 5,229,348; 6,231,660; 6,375,969; 6,416,775; and 6,613,138. An example of suitable commercially available inert granule substrate materials based on ground peanut hulls that are useful in the stabilized pesticidal compositions of the invention are the BIO 170 Granules™ available from Bio Plus, Inc. (Madison, Ga.). Preferred inert materials for use as the granular substrate are dried clay, calcium carbonate, dolomite, ground corn cobs, peanut hulls and bentonite clay.

As used herein, the term "fertilizer material" is defined as any substance capable of supplying plant nutrients or minerals, e.g., primary (N—P—K) or secondary (Ca—Mg—S) macronutrients, and/or micronutrients (B, Cu, Fe, chloride, Mn, Mo and Zn) to vegetation.

Among the suitable fertilizer materials that can be used to formulate the granular substrate include, but are not limited to, water-soluble and water-insoluble materials, like ammonium sulfate, ammonium chloride, ammonium nitrate, an ammonium phosphate, sodium nitrate, potassium nitrate, calcium nitrate, potassium chloride, potassium sulfate, potassium carbonate, a sodium phosphate, a potassium phosphate, urea, methyleneurea, compounds capable of providing vegetation a micronutrient, such as copper, magnesium, zinc, calcium, boron, molybdenum, manganese, iron, and nickel, magnesium sulfate, an iron chelate, manganese sulfate, nickel sulfate, zinc sulfate, copper sulfate, animal dung fertilizers, organic fertilizers, and mixtures thereof.

In addition to urea and methyleneurea, other types of bio-available nitrogen compounds that can be used in suitable urea based fertilizer containing granular substrates include a methyleneurea oligomer or a mix of methyleneurea oligomers as represented by the formula $NH_2CONH(CH_2NHCONH_2)_nH$, where n is an integer from 1-10. Such methyleneurea oligomers include methylenediurea ($NH_2CONHCH_2NHCONH_2$), dimethylenetriurea ($NH_2CONHCH_2NHCONHCH_2NHCONH_2$), trimethylenetetraurea and tetramethylenepentaurea. Certain suitable mix of methyleneurea oligomers are commercially available such as: Nutralene® by Nu-Gro Technologies, Canada, Methex-40 by Homestead Corporation and as Nitroform®.

It has been observed that certain fertilizers such as urea based fertilizers contain nucleophilic components that can react with and destabilize 2-(2'-nitro-4'-methylsulphonylbenzoyl)-1,3-cyclohexanedione acid when present in granular formulations. In accordance with one aspect of the invention, it has been discovered that metal chelates of 2-(2'-nitro-4'-methylsulphonylbenzoyl)-1,3-cyclohexanedione are substantially stable and substantially not reactive with such nucleophilic components in granular fertilizer formulations.

Accordingly, the present invention provides a stabilized granular composition for control of weeds, which composition comprises 2-(2'-nitro-4'-methylsulphonylbenzoyl)-1,3-cyclohexanedione and a nucleophilic component containing fertilizer, the 2-(2'-nitro-4'-methylsulphonylbenzoyl)-1,3-cyclohexanedione being provided in the form of a chelate with a di- or tri-valent metal ion which prevents or reduces interaction between the 2-(2'-nitro-4'-methylsulphonylbenzoyl)-1,3-cyclohexanedione and the nucleophilic component containing fertilizer in the granular composition.

Nitrogen, oxygen, metal ions, and micronutrients may all serve as examples of nucleophiles. Particular nitrogen nucleophiles which may be mentioned include urea, methyleneurea, the above-mentioned methyleneurea oligomers as well as any free ammonia which may be present in the fertilizer from, for example, the monoamino- or diaminophosphates.

Suitable fertilizer granule substrates include straight fertilizers (those containing only one nutrient), compound fertilizers (those containing two or more nutrients), complex fertilizers (compound fertilizer formed by mixing ingredients that react chemically), prilled fertilizers (a granular fertilizer of near-spherical form made by solidification of free-falling droplets in air or other fluid medium (e.g., oil)), coated fertilizers (granular fertilizer that has been coated with a thin layer of some substance to prevent caking or to control dissolution rate), conditioned fertilizers (a fertilizer treated with an additive to improve physical condition or prevent caking), and bulk-blend fertilizers (two or more granular fertilizers mixed together to form a compound fertilizer, including those having granules of a similar size). Suitable substrates also include manufactured homogeneous fertilizers, blended fertilizers and granular pesticides.

Specific commercially available examples of a suitable fertilizer granular substrate materials on which to apply at least one metal chelate of 2-(2'-nitro-4'-methylsulphonylbenzoyl)-1,3-cyclohexanedione include the Professional Turf™ and Contec™ Methylene Urea Fertilizer lines of fertilizer granules available from The Andersons, Inc. (Maumee, Ohio) and The Scotts Company (Marysville, Ohio) Turfbuilder® line of fertilizer granules.

The granular substrate material also can contain various optional ingredients known to persons skilled in the art. For example, auxiliaries such as binders, adjuvants, rewetting agents, disintegration aids, de-dusting agents, stabilizers, surfactants, dyes, and similar optional ingredients can be included to provide stabilized pesticidal compositions that are safely handled and convenient to apply accurately to areas in need of treatment. Furthermore, other pesticides (e.g., herbicides, insecticides, fungicides or growth regulators) can also be present on or within the granular substrate.

Illustrative examples of binders useful in the preparation of suitable granular substrates are carbohydrates such as monosaccharides, disaccharides, oligosaccharides and polysaccharides; proteins; lipids; glycolipid; glycoprotein; lipoprotein; and combinations and derivatives of these.

The granular substrates of this invention can be manufactured according to known methods, such as by preparing (dry blending and/or spraying) a homogeneous bulk mixture of components, pelletizing the mixture, drying and then screening the granules to a desired size. For example, a conventional production method for a pesticidal granule may be used, such as an extrusion granulator, compression granulator, stirring granulator, pan granulator, fluidized bed granulator, disc pelletizer, paddle mixer, drum granulator, pin mixer and the like, and the granulation is generally conducted to obtain a granule having a diameter from 0.1 to about 30 mm, particularly from 0.25 to 20 mm. One skilled in the art of pelletizing/granulation is capable of recognizing the variables and making adjustments to obtain a granular substrate material having the desired properties without undue experimentation.

Suitable granules can be in virtually any desired shape, for example, spheres, cylinders, ellipses, rods, cones, discs, needles and irregular shapes. Ideally, the granules are approximately spherical and have a smooth surface, which lends to desired flow characteristics of the granules in bulk form.

The granules typically have a particle size in the range of about 0.1 to about 30 mm, particularly between about 0.25 to about 20 mm, and more particularly between about 0.5 to about 15 mm, although sizes outside of this range can be used.

In accordance with the invention, at least one metal chelate of 2-(2'-nitro-4'-methylsulphonylbenzoyl)-1,3-cyclohexanedione is associated with a particle during the process of granule formation and homogeneously distributed throughout the granule (extrusion granulator) or is spray impregnated or absorbed onto the granule substrate after the granules are formed.

Where it is desirable to add the at least one metal chelate of 2-(2'-nitro-4'-methylsulphonylbenzoyl)-1,3-cyclohexanedione after particle formation, the metal chelate of 2-(2'-nitro-4'-methylsulphonylbenzoyl)-1,3-cyclohexanedione (and any other optional liquid or solid active ingredients) are added to the granular substrate following particle formation in the presence or absence of an adhesive or sticker. Methods of 2-(2'-nitro-4'-methylsulphonylbenzoyl)-1,3-cyclohexanedione metal chelate impregnation illustratively include spraying onto the granular substrate or adsorption of the metal chelated 2-(2'-nitro-4'-methylsulphonylbenzoyl)-1,3-cyclohexanedione by coating the granule with a suspension of the metal chelate of 2-(2'-nitro-4'-methylsulphonylbenzoyl)-1,3-cyclohexanedione.

The stabilized pesticide composition of the invention may be prepared by using a millbase of the metal chelate of 2-(2'-nitro-4'-methylsulphonylbenzoyl)-1,3-cyclohexanedione as a spray solution for spray impregnating, coating or absorbing the chelate material onto a suitable granule substrate. Suitable millbases for use in this invention may be prepared by the methods described in the PCT application WO 2005/055714 (the disclosure of which is incorporated herein by reference), or by the application and adaptation of known methods used or described in the chemical literature. For example, water, acetic acid, a non-ionic surfactant and the 2-(2'-nitro-4'-methylsulphonylbenzoyl)-1,3-cyclohexanedione are mixed together. A stabilizing agent (e.g., copper hydroxide) is then added. An antifoaming agent is added along with an optional thickener (e.g., xanthan gum) and/or adjuvant (e.g., ammonium nitrate) are added and mixed until uniform. If needed, the millbase is milled to the desired particle size.

Nonionic surfactants which can be used to prepare suitable millbases are, for example, the ethoxylated arylalkylphenols, particularly ethoxylated tristyrylphenol having a mean EO chain length in the range from 10 to 80 EO, more particularly from 16 to 40 EO, such as, for example, the products Soprophor BSU, Soprophor CY/8, Soprophor S/25 or Soprophor S/40-P available from Rhodia.

In one embodiment, a mixture of a metal chelate of 2-(2'-nitro-4'-methylsulphonylbenzoyl)-1,3-cyclohexanedione with a second solid pesticidally active ingredient is adhered to the outside surface of the granular substrate with the use of an adhesive or sticker. An adhesive liquid may be used and is applied before or after the addition of the solid active ingredient or it may be applied at the same time as the solid active ingredient. The choice of adhesive depends on the granule substrate components and will be evident to one skilled in the art. Examples of a liquid adhesive include but are not limited to binders listed herein, including mineral oils or polymer liquids such as polybutene.

Those of skill in the art can readily determine how much metal chelate 2-(2'-nitro-4'-methylsulphonylbenzoyl)-1,3-cyclohexanedione to add to the granules. For example, one can simply consider the application rate of the granules in their intended use (for example, as a fertilizer having a particular N—P—K rating), and the application rate of metal chelate 2-(2'-nitro-4'-methylsulphonylbenzoyl)-1,3-cyclohexanedione as a herbicide, and determine an appropriate ratio by which to add the metal chelate of 2-(2'-nitro-4'-methylsulphonylbenzoyl)-1,3-cyclohexanedione to the granules.

For example, the amounts of individual ingredients can vary widely, with at least one 2-(2'-nitro-4'-methylsulphonylbenzoyl)-1,3-cyclohexanedione metal chelate generally being present in an amount from about 0.02 to about 60 percent by weight of (on an acid equivalent basis), particularly between about 0.05 to about 1.0 percent by weight, and more particularly from about 0.1 to 0.6, for example around 0.25 percent by weight of the pesticidal composition. In one embodiment, the "filler" (non pesticidally active constituents) generally comprises about 10 to about 90 percent by weight, the surface active agent generally about 0 to about 20 percent by weight, and an auxiliary agent generally about 0.01 to about 10 percent by weight of the pesticidal composition, although weight ranges outside of these ranges can be used. The granular pesticidal compositions can also be prepared without one or more of a filler, surfactant or auxiliary agent.

The granules containing a 2-(2'-nitro-4'-methylsulphonylbenzoyl)-1,3-cyclohexanedione metal chelate according to the invention can also be produced as premixes with other herbicides, or can be blended with one or more additional herbicidal or other agricultural compositions.

Specific examples of other herbicides which may be incorporated in a granular herbicidal composition with the 2-(2'-nitro-4'-methylsulphonylbenzoyl)-1,3-cyclohexanedione metal chelates according the invention include 2,4-D, aminopyralid, asulam, atrazine, benefin, bensulide, bentazon, bispyribac, bromoxynil, carfentrazone, chlorsulfuron, clopyralid, dicamba, diquat, dithiopyr, fenoxaprop p-ethyl, floramsulfuron, fluazifop-p-butyl, flumioxaden, fluoroxypyr, halosulfuron, hexazinone, imazaquin, isoxaben, mefluidide, methanearsonate, metolachlor, s-metolachlor, metsulfuron, metsulfuron-methyl, oxadiazon, pendimethalin, pinoxaden, prodiamine, pronamide, quinclorac, rimsulfuron, siduron, sulfentrazone, sulfosufuron, triclopyr, trifloxysulfuron, trinaxepac-ethyl, trinaxepac-ethyl.

Among the suitable co-herbicides there may be mentioned s-metolachlor, dicamba, bentazone, prodiamine, sulfentrazone, carfentrazone-ethyl, atrazine, simazine, and triclopyr.

As noted above, the at least one 2-(2'-nitro-4'-methylsulphonylbenzoyl)-1,3-cyclohexanedione metal chelate can be homogeneously distributed throughout the granule, spray impregnated, absorbed or coated onto the granules.

Method of Use

The stabilized pesticidal composition of the invention may be used against a large number of agronomically important weeds, including, but not limited to: Stellaria, Nasturtium, Agrostis, Digitaria spp. (e.g., D. ischaemum, D. sanguinalis), Avena, Setaria, Sinapis, Lolium, Solanum, Phaseolus, Echinochloa, Scirpus, Monochoria, Sagittaria, Taraxacum officinale; Trifolium repens; Bromus, Alopecurus, Sorghum halepense, Rottboellia, Cyperus, Abutilon, Sida, Xanthium, Amaranthus, Chenopodium, Ipomoea, Chrysanthemum, Galium, Viola, and Veronica.

Among the weeds which may be controlled by the stabilized pesticidal composition of the invention there may be mentioned large and smooth crabgrass, dandelion, white and red clover, chickweed, henbit, corn speedwell, oxalis, nimblewill, bent grass, buckhorn and broadleaf plantain, dollar weed, FL pusley, lambsquarters, knotweed, ragweed, wild violets, pigweed and hedge weed. Weeds that are not killed are often stunted, non-competitive, with flowering disrupted.

For purposes of the present invention, the term "weeds" includes undesirable crop species such as volunteer crops. For example, in the context of turf grass crops such as on a golf course, creeping bentgrass putting green turf can be considered a "volunteer" if found in a fairway section where a different variety of grass is being cultivated.

Controlling means killing, damaging, or inhibiting the growth of the weeds. The "locus" is intended to include soil, seeds, and seedlings, as well as established vegetation.

The benefits of the present invention are seen most when the stabilized pesticidal composition is applied to kill weeds in growing crops of useful plants: such as maize (corn) including field corn, pop corn, and sweet corn; asparagus, bushberries (blueberries), caneberries, cranberries, flax, grain sorghum, oakra, oats, peppermint, rhubarb, spearmint and sugarcane.

"Crops" are to be understood to also include various turf grasses including the cool-season turf grasses (at seeding or to established annual ryegrass, fine fescue, Kentucky bluegrass, perennial ryegrass, tall fescue) and warm-season turf grasses (centipede, hybrid bermudagrass, and St. Augustinegrass. There may also be mentioned common bermuda and zoysiagrass).

In addition, "crops" are to be understood to include those crops that have been made tolerant to pests and pesticides, including herbicides or classes of herbicides, as a result of conventional methods of breeding or genetic engineering. The benefit of the invention is seen most with post-emergent application, but pre-emergent application is also possible.

In one embodiment, the stabilized pesticidal composition of the invention is applied to the locus where control is desired by a convenient method (i.e., postemergent application) in the form of dry spreadable granules. The stabilized pesticidal composition of the invention is applied in an amount sufficient to assure herbicidal action. The amount applied depends on the amount of metal chelated 2-(2'-nitro-4'-methylsulphonylbenzoyl)-1,3-cyclohexanedione in the granular herbicidal composition and the purpose for which it is being used.

In one embodiment, the stabilized pesticidal composition of the invention is applied as granules that retain their physical integrity when spread, and typically disintegrate when irrigation water is applied or rainfall hits the particle. Upon wetting, the granules disintegrate (bloom) to cover the soil surface. This bloom can cover an area many times the original area covered by the granule.

Particularly when used as a fertilizer as well as an herbicide, the granules can be typically applied in the range of about 150 to about 300 particles per square foot. Although liquid spray herbicidal formulations can provide a higher percentage of weed control than granular applications, it has been found that the use of a smaller particle size, for example, about 1 mm granules, can provide results which are comparable to that obtained using liquid spray application.

Formulations containing the metal chelates of 2-(2'-nitro-4'-methylsulphonylbenzoyl)-1,3-cyclohexanedione can be applied by conventional methods to the areas where control is desired. For example, the stabilized pesticidal composition of the invention in the form of granules can be applied with a dry spreader, such as a rotary spreader, to a target area. The granules can then be dispersed by water, whether user-applied or natural, such as rain, dew or atmospheric humidity. When exposed to water via, for example, rain or irrigation, the granules can not only readily disintegrate, but can actively spread on solid substrates.

In the practice of the present invention, the metal chelate of 2-(2'-nitro-4'-methylsulphonylbenzoyl)-1,3-cyclohexanedione is applied postemergent to the locus of the undesirable vegetation to be controlled. Application rates will depend on the particular plant species and degree of control desired. In general, application rates of between about 5 and about 500 g/ha (acid equivalent) may be employed. For example, the compositions can be applied in an amount such that the 2-(2'-nitro-4'-methylsulphonylbenzoyl)-1,3-cyclohexanedione is applied at a rate of 20-300 g a.i./ha, suitably 40-250 g a.i./ha (acid equivalent).

In one embodiment, sufficient amounts of the stabilized pesticidal composition of the invention in the form of granules can be applied to achieve a 2-(2'-nitro-4'-methylsulphonylbenzoyl)-1,3-cyclohexanedione (acid equivalent) application rate of from 0.1 to 1.5 lbs a.i./A; more particularly from 0.1 to 0.80 lbs a.i./A; and most particularly from 0.15 to 0.5 lbs a.i./A. A rate of 0.2-0.25 lbs a.i./A is often suitable.

EXAMPLES

The following are additional examples of the present invention.

Example 1

An a.i. copper chelate spray solution is prepared in the following way:

| Formulation Ingredients | % WT |
| --- | --- |
| A.I.: 2-(2'-nitro-4'-methylsulphonylbenzoyl)-1,3-cyclohexanedione | 28 |
| Surfactant: (ethoxylated tristyrylphenol) (80% form) | 3.6 |
| Acetic Acid | 9 |
| Copper Hydroxide | 4 |
| Antifoam (polydimethylsiloxane) | 0.1 |
| Ammonium Nitrate | 4.3 |
| Water | 49 |

Water, antifoam and surfactant are charged to a suitably sized mixing vessel and mixed until uniform. Acetic acid is then added and mixed until uniform to a pH of about 2.3. The 2-(2'-nitro-4'-methylsulphonylbenzoyl)-1,3-cyclohexanedione is added under agitation and mixed until uniform while maintaining pH. At this point vigorous mixing is employed using a high shear mixer. The copper hydroxide is added slowly over a period of from 1.5 to 2 hours while maintaining temperature between 25-35° C. and allowing pH to rise to a maximum of 4.0. Ammonium nitrate is then added and blended until homogeneus. The resultant suspension of 2-(2'-nitro-4'-methylsulphonylbenzoyl)-1,3-cyclohexanedione copper chelate is milled to remove course material and resuspended prior to use. If a batch larger than about 5 gallons is prepared, the reaction mixture is advantageously "seeded" at the outset with an about 5% by weight of a 2-(2'-nitro-4'-methylsulphonylbenzoyl)-1,3-cyclohexanedione copper chelate from a previous batch.

Example 2

Preparation of Herbicide Granules

A suitable amount of ground peanut hulls (BIO 170 Granules™) is charged to mixer while mixing. The inert granular substrate material is sprayed with a requisite amount of spray solution prepared in accordance with Example 1 to achieve an average a.i. loading of 0.32% by weight. A flow aid (HiSil, for example) is also charged to the mixer as needed to decrease stickiness/tackiness of the stabilized pesticidal composition.

Example 3

The procedure of Example 2 is repeated, except that Callisto® (a commercially available liquid formulation containing 4 lbs/gal of the active ingredient 2-(2'-nitro-4'-methylsulphonylbenzoyl)-1,3-cyclohexanedione acid) (Syngenta Crop Protection, Inc.) is used in lieu of the spray solution of Example 1 in amount sufficient to achieve an average a.i. loading of 0.23% by weight.

Example 4

The procedure of Example 1 is repeated, except that ground corn cobs are used as the inert granular substrate material and sprayed with an amount of the spray solution of Example 1 sufficient to achieve an average a.i. loading of 0.67% by weight.

Example 5

The procedure of Example 4 is repeated, except that Callisto is used in lieu of the spray solution of Example 1 in amount sufficient to achieve an average a.i. loading of 0.24% by weight.

Example 6

The procedure of Example 1 is repeated, except that fertilizer granules (Scotts® Turf Builder® Lawn Fertilizer 29-3-4 (with added nutrients)) (The Scotts Co.) are used as the granular substrate material and sprayed with an amount of the spray solution of Example 1 sufficient to achieve an average a.i. loading of 0.28% by weight.

Example 7

The procedure of Example 6 is repeated, except that Callisto is used in lieu of the spray solution of Example 1 in amount sufficient to achieve an average a.i. loading of 0.16% by weight.

Example 8

Stability Comparison

The materials prepared in examples 1-7 are tested for stability as follows:
1) After obtaining the coated granules according to the procedures given above, material is divided up into samples by using a standard "Riffler", which is used to generate statistically representative samples from a large batch.
2) The individual "riffled" samples are put on accelerated temperature storage (in ovens) at 38° C. and 50° C.
3) Samples are pulled from each temperature at regular intervals, and assayed for 2-(2'-nitro-4'-methylsulphonylbenzoyl)-1,3-cyclohexanedione acid concentration (weight %). Commonly 2-3 samples are pulled from each temperature, each week.
4) The pulled samples are analyzed for stability by extraction of the a.i. material from the granules and assayed by HPLC.

The results are given in the tables shown below.

TABLE 1

Comparison of Examples 2 and 3-
Chelate vs. Acid on BIO 170

| | % (38° C.) | | % (50° C.) | |
|---|---|---|---|---|
| Time (days) | Chelate | Acid | Chelate | Acid |
| 0 | 0.323 | 0.234 | 0.323 | 0.234 |
| 2 | 0.3541 | 0.217 | 0.3432 | 0.302 |
| 9 | 0.3516 | 0.263 | 0.3444 | 0.223 |
| 12 | 0.3372 | 0.213 | 0.3442 | 0.157 |
| 19 | 0.34 | 0.197 | 0.34 | 0.12 |
| 23 | 0.33 | 0.209 | 0.33 | 0.082 |
| 26 | 0.35 | 0.268 | 0.35 | 0.088 |
| 28 | 0.35 | 0.193 | 0.33 | 0.084 |

TABLE 2

Comparison of Examples 6 and 7-
Chelate vs. Acid on Turf Builder

| | % (38° C.) | | % (50° C.) | |
|---|---|---|---|---|
| Time (days) | Chelate | Acid | Chelate | Acid |
| 0 | 0.282 | 0.163 | 0.282 | 0.163 |
| 7 | 0.281 | 0.152 | 0.27 | 0.085 |
| 12 | 0.298 | 0.15 | 0.267 | 0.052 |
| 14 | 0.278 | 0.148 | 0.255 | 0.036 |
| 19 | 0.272 | 0.133 | 0.246 | 0.025 |
| 21 | 0.278 | 0.129 | 0.238 | 0.019 |
| 26 | 0.276 | 0.128 | 0.224 | 0.011 |
| 28 | 0.274 | 0.155 | 0.219 | 0.008 |

The above data indicates that the copper chelate of 2-(2'-nitro-4'-methylsulphonylbenzoyl)-1,3-cyclohexanedione showed improved stability over the unchelated (acid) form of the active ingredient on granules.

Example 9

Biology Comparison

Callisto® (a commercially available liquid formulation containing 4 lbs/gal of the active ingredient 2-(2'-nitro-4'-methylsulphonylbenzoyl)-1,3-cyclohexanedione acid) (Syngenta Crop Protection, Inc.) is sprayed onto fertilizer granules (Scotts® Turf Builder® Lawn Fertilizer 29-3-4 (with added nutrients)) (The Scotts Co.) in an amount sufficient to achieve an average a.i. loading of 0.082% by weight. Sample 2 is a control sample that is freshly prepared and has not been stored. Sample 3 is stored for 1 year at ambient room temperature. Sample 4 is stored under accelerated conditions (19 days at 50° C.).

A spray solution of Example 1 is sprayed onto fertilizer granules (Scotts® Turf Builder® Lawn Fertilizer 29-3-4 (with added nutrients)) (The Scotts Co.) in an amount sufficient to achieve an average a.i. loading of 0.082% by weight. Sample 5 is stored for 1 year at ambient room temperature. Sample 6 is stored under accelerated conditions (19 days at 50° C.).

All samples are applied to large crabgrass (*Digitaria sanguinalis*) at 224 g ai/ha, and control assessed 10 days after treatment. Sample 1 is an untreated control.

The results are presented in Table 3 below.

TABLE 3

| Sample | Percentage control at 10DAT |
|---|---|
| 1 | 0 |
| 2 | 63 |
| 3 | 43 |
| 4 | 33 |
| 5 | 58 |
| 6 | 52 |

The above data indicates that, after storage for 1 year at room temperature, or accelerate storage conditions (19 days at 50° C.), the copper chelate of 2-(2'-nitro-4'-methylsulphonylbenzoyl)-1,3-cyclohexanedione on fertiliser granules showed improved control of large crabgrass over the unchelated (acid) form of the active ingredient on fertiliser granules.

The foregoing description and examples are for the purpose of illustration only and do not limit the scope of protection which should be accorded this invention.

What is claimed is:

1. An improved stability and prolonged storage pesticidal composition comprising at least one granular substrate material wherein at least one metal chelate, selected from the group consisting of copper chelate, cobalt chelate, zinc chelate, nickel chelate, and calcium chelate, of 2-(2'-nitro-4'-methylsulphonylbenzoyl)-1,3-cyclohexanedione is applied to a surface of said granular substrate, wherein said granular substrate comprises a fertilizer material and wherein said granular substrate material has improved stability and prolonged storage over a granular fertilizer substrate material with a surface treated with an unchelated form of 2-(2'-nitro-4'-methylsulphonylbenzoyl)-1,3-cyclohexanedione.

2. The composition according to claim 1, wherein the granular substrate material contains a fertilizer comprising at least one plant micronutrient selected from boron, copper, iron, chloride, manganese, molybdenum and zinc.

3. The composition according to claim 1, wherein the granular substrate material contains a fertilizer selected from a urea, a methylene urea oligomer and a mix of methylene urea oligomers as represented by the formula $NH_2CONH(CH_2NHCONH_2)_nH$, where n is an integer from 1-10.

4. The composition according to claim 1, wherein the fertilizer material is a straight fertilizer.

5. The composition according to claim 1, wherein the fertilizer material is a compound fertilizer.

6. The composition according to claim 1, wherein the fertilizer material is a complex fertilizer.

7. The composition according to claim 1, wherein the fertilizer material is a prilled fertilizer.

8. The composition according to claim 1, wherein the fertilizer material is a coated fertilizer.

9. The composition according to claim 1, wherein the fertilizer material is a conditioned fertilizer.

10. The composition according to claim 1, wherein the fertilizer material is a bulk-blend fertilizer.

11. The composition according to claim 1, which further comprises a herbicide selected from s-metolachlor, dicamba, bentazone, prodiamine, sulfentrazone, carfentrazone-ethyl, atrazine, simazine, and triclopyr.

12. A method of controlling large crabgrass or said smooth crabgrass in a crop of useful plants which comprises applying a herbicidally effective amount of a pesticidal composition comprising at least one granular substrate material to the locus of said large crabgrass or said smooth crabgrass wherein at least one metal chelate, selected from the group consisting of copper chelate, cobalt chelate, zinc chelate, nickel chelate, and calcium chelate, of 2-(2'-nitro-4'-methylsulphonylbenzoyl)-1,3-cyclohexanedione is applied to a surface of said granular substrate, and wherein said granular substrate material has improved control of said large crabgrass or said smooth crabgrass over a granular fertilizer substrate material having its surface treated with an unchelated form of 2-(2'-nitro-4'-methylsulphonylbenzoyl)-1,3-cyclohexanedione being applied to said crabgrass.

13. The method of claim 12 wherein the crop is maize.

14. The method of claim 12 wherein the crop is selected from asparagus, bushberries (blueberries), caneberries, cranberries, flax, grain sorghum, oakra, oats, peppermint, rhubarb, spearmint and sugarcane.

15. The method of claim 12 wherein the crop is a turf grass.

16. The method of claim 15 wherein the turf grass is selected from cool-season turf grasses and warm-season turf grasses.

* * * * *